United States Patent [19]

LaConti et al.

[11] Patent Number: 4,820,386

[45] Date of Patent: Apr. 11, 1989

[54] DIFFUSION-TYPE SENSOR CELL CONTAINING SENSING AND COUNTER ELECTRODES IN INTIMATE CONTACT WITH THE SAME SIDE OF A PROTON-CONDUCTING MEMBRANE AND METHOD OF USE

[75] Inventors: Anthony B. LaConti, Lynnfield; Arthur E. Griffith, Lynn, both of Mass.

[73] Assignee: Giner, Inc., Waltham, Mass.

[21] Appl. No.: 151,937

[22] Filed: Feb. 3, 1988

[51] Int. Cl.[4] ...................... G01N 27/28; G01N 27/54

[52] U.S. Cl. .................................... 204/1 T; 204/412

[58] Field of Search ............... 204/412, 431, 432, 1 B, 204/1 K

[56] References Cited

U.S. PATENT DOCUMENTS

| | | | |
|---|---|---|---|
| 4,123,700 | 10/1978 | LaConti et al. | 324/29 |
| 4,171,253 | 10/1979 | Nolan et al. | 204/412 X |
| 4,227,984 | 10/1980 | Dempsey et al. | 204/1 T X |
| 4,265,714 | 5/1981 | Nolan et al. | 204/1 T |
| 4,591,414 | 5/1986 | Zaromb et al. | 204/1 T |
| 4,707,242 | 11/1987 | Schneider et al. | 204/412 |

*Primary Examiner*—G. L. Kaplan

*Attorney, Agent, or Firm*—A. W. Breiner

[57] ABSTRACT

A fast response diffusion-type sensor cell for the detection of carbon monoxide and other oxidizable or reducible gases comprising a three-electrode hydrated proton-conducting membrane cell configuration, with all electrodes in intimate contact with the same proton-conducting membrane is described. The liquid electrolyte-free system has a porous gas-diffusion sensing electrode and a counter electrode located on the same side of and in intimate contact with the proton-conducting membrane. The reference electrode is spatially located on the same or opposite side of the membrane as are the sensing and counter electrodes. The cell configuration is advantageous in that (1) the ionic resistance value between the sensing/reference electrodes is lower than that between the sensing/counter electrodes, and (2) the sensing and counter electrodes being on the same side of the membrane and connected by one or more hydrated proton-exchange membrane channels leads to faster response times and greater immunity to interference from counter electrode reaction products.

27 Claims, 2 Drawing Sheets

16 2 4 3 31 26 30 22 24 H2O 14 RESERVOIR 18 20 32 36 34 44 46 CO, CO2 OUT CO2 IN GAS FLOW CHAMBER 40 10

16
2
4
3
46
44
31
CO, $CO_2$ OUT
26
30
$H_2O$
14
22
24
RESERVOIR
32
36
34
18
20
$CO_2$ IN
46
44
4
2
3
10
GAS FLOW CHAMBER
40

20
24
26

20
22

18

32
40
38
36

26
24
22
20

POROUS DISK 32
DIFFUSION TUBE 30 WITH INSERT 34
14
H2O
REF ELECTRODE
22
H+
H2O
SOLID POLYMER ELECTRO-LYTE MEMBRANE
20
CO
SENSOR ELECTRODE
24
CO2
L
CO
36
CO2
d
26
31
COUNTER ELECTRODE AIR DIFFUSION HOLE
COUNTER ELECTRODE 57.0 μA
56.0 μA
90% RESPONSE @ t=0.18 min.
(160 ppm CO; 70 cc/min.)
10.2 μA
i (μa)
0
1
2
3
4
5
6
1"
CHART SPEED (1"/min.)
RESPONSE - TIME CURVE (DIFFUSION CELL A)

DIFFUSION-TYPE SENSOR CELL CONTAINING SENSING AND COUNTER ELECTRODES IN INTIMATE CONTACT WITH THE SAME SIDE OF A PROTON-CONDUCTING MEMBRANE AND METHOD OF USE

FIELD OF INVENTION

This invention is directed to a sensor cell comprising a proton-conducting solid polymer electrolyte for the detection of carbon monoxide, hydrogen, and other easily oxidizable or reducible gases and vapors. More particularly, the invention is directed to a sensor cell of the diffusion type comprising a proton-conducting solid polymer electrolyte and a porous gas-diffusion sensing electrode and a counter electrode located on the same side of, and in intimate contact with the proton-conducting solid polymer electrolyte.

BACKGROUND OF INVENTION

Gas sensors for the detection of carbon monoxide, hydrogen, and other easily oxidizable gases and vapors utilizing a proton-conducting solid polymer electrolyte are disclosed in LaConti et al, U.S. Pat. Nos. 4,123,700; 4,171,253, and 4,227,984. These sensors are also described in "Electrochemical Detection of $H_2$, CO, and Hydrocarbons in Inert or Oxygen Atmospheres" by LaConti et al, *Journal Of The Electrochemical Society*, Vol. 118, No. 3, Mar. 1971, pages 506–510, hereinafter "Journal"; "Recent Developments in Electrochemical Solid Polymer Electrolyte Sensor Cells for Measuring Carbon Monoxide and Oxides of Nitrogen" by LaConti et al, *ACS Symposium Series*, No. 149, Chemical Hazards in the Workplace--Measurement and Control, *American Chemical Society*, pages 552–573, 1981; and "Development of SPE Diffusion Head Instrumentation" J. A. Kosek et al, *Proceedings: National Symposium on Recent Advances in Pollutant Monitoring of Ambient Air and Stationary Sources*, Raleigh, N.C., May 4–7, 1982, EPA-600/9-83-007 May 1983, pages 333–357. One of the unique features claimed for the cells such as described in the aforesaid disclosures is that the sensing and reference electrodes are located on the same side of the membrane. The electrodes are so positioned that the ionic resistance path between the sensing and reference electrodes is greater than 60 ohms as described in the '984 patent. Furthermore, the sensing to reference electrode resistance is high compared to the sensing and counter electrodes resistance with the ratio being greater than 50 to 1. This spatial arrangement places the reference electrode outside of the current flux lines between sensing and counter electrodes.

Although the sensor cells disclosed by LaConti et al are advantageous, there are disadvantages in that the response time is relatively slow (100 to 200 seconds) and there can be potential interference caused by permeation to the sensor electrode of the hydrogen gas generated at the counter electrode. This is of special concern when detecting higher concentrations of oxidizable gases such as CO, $H_2$, alcohol, and the like, according to the following scheme illustrated with respect to CO:

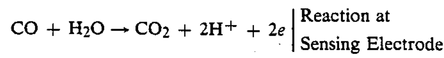
$$CO + H_2O \rightarrow CO_2 + 2H^+ + 2e \quad \text{Reaction at Sensing Electrode}$$

-continued

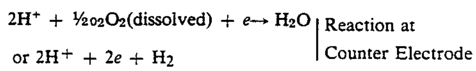
$$2H^+ + \tfrac{1}{2}O_2(\text{dissolved}) + e \rightarrow H_2O \text{ or } 2H^+ + 2e + H_2 \quad \text{Reaction at Counter Electrode}$$

Generally there is some dissolved $O_2$ (from air) at the counter electrode present in the water in the cell reservoir. The dissolved oxygen at the counter electrode is rapidly consumed when detecting typical CO concentration levels, i.e., greater than about 50 ppm, for any substantial period of time and the counter electrode proceeds to hydrogen evolution. The permeation of this generated hydrogen from counter to sensing electrodes increases with (1) increasing CO concentration, i.e., with $H_2$ generated at a faster rate; (2) increasing membrane water content, and (3) decreasing membrane thickness.

It is difficult to alter the membrane properties in these liquid-free membrane sensor cells without affecting structure and response level.

SUMMARY OF THE INVENTION

The present invention is directed to a fast response diffusion-type sensor cell for detection of oxidizable or reducible gases which are free or substantially free of the disadvantages of the aforesaid LaConti et al type cells. The sensor cell comprises a three-electrode hydrated proton-conducting membrane cell configuration with all electrodes in intimate contact with the same liquid electrolyte-free proton-conducting membrane wherein a porous gas diffusing sensing electrode and a counter electrode are located on the same side of and in intimate contact with the proton-conducting membrane. The reference electrode, also in intimate contact with the same membrane, is preferably spatially located on the opposite side of the membrane directly across from the sensing membrane. However, the reference electrode can be located on the same side of the membrane as are the sensing and counter electrodes.

It has been found that the cell configuration wherein the sensing electrode and the counter electrode are located on the same side of the proton-conducting membrane provides unique results in that (1) the ionic resistance value between the sensing/reference electrode is lower than that between the sensing/counter electrode; and (2) the sensing and counter electrodes on the same side of the membrane are connected by one or more hydrated proton-exchange membrane channels. This configuration leads to faster response times and greater immunity to interference from counter electrode reaction products.

GENERAL DESCRIPTION OF THE INVENTION

The gas sensor cells of the present invention will be described in reference to the drawings wherein.

Figure 1:
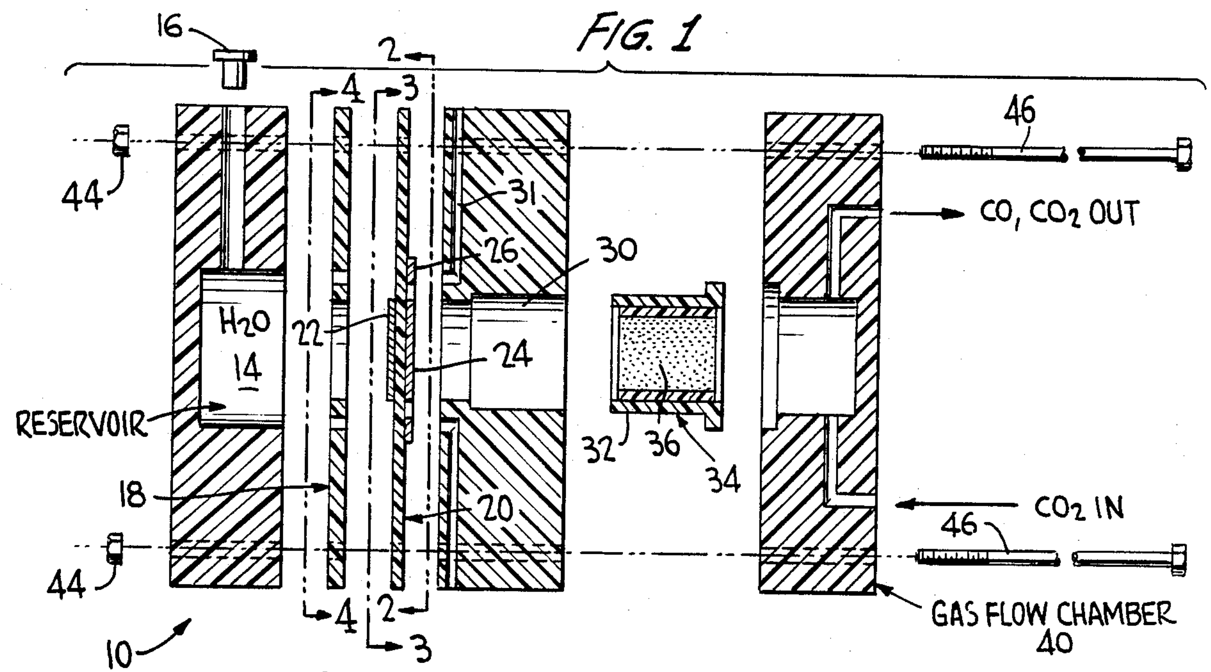
FIG. 1 is an expanded, sectional view of a gas sensor cell according to the present invention.

Referring primarily to FIGS. 1-5, the sensor cell 10 of the invention comprises a reservoir having a chamber 14 for holding water and a cap 16 for closing off chamber 14; a perforated separator/gasket assembly 18, a proton-conducting membrane 20, having a reference electrode 22 on one side of membrane 20 and a sensing electrode 24 directly opposite of the reference electrode on the other surface of membrane 20. A counter electrode 26 surrounds sensing electrode 24 on the same surface of membrane 20. The cell further includes a diffusion tube 30 having an insert 34 which forms compartments separating the counter and sensing electrodes from each other and which aids in the diffusion of the gases being sensed. The cell, for calibration, can include a gas flow chamber 40. The components of the cell are secured together with nuts 44 and bolts 46.

Figure 2:
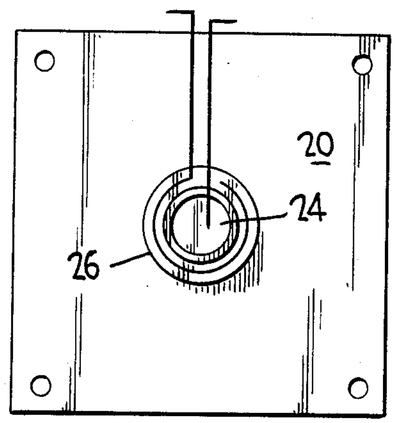
FIG. 2 is a plane view of one side of the proton-conducting membrane showing the sensing and counter electrodes utilized in the cell of FIG. 1.

The sensing electrode 24, best shown in FIG. 2, having a diameter of approximately 0.79 cm (0.31"), is bonded to one surface of hydrated proton-conducting membrane 20 with a thickness of approximately 0.02 cm (0.009"). Circular counter electrode 26, also as best shown in FIG. 2, having an inner diameter of 1.11 cm (0.44") and an outer diameter of 1.59 cm (0.63"), is bonded to the same side of membrane 20 in a pattern that encircles the smaller diameter sensing electrode 24. The distance between the sensing and counter electrode edges is approximately 0.24 cm (0.095"). The sensing and counter electrodes are in separate compartments formed by the diffusion tube 30 and gasket sealed from each other so that there is no leakage of gases or vapors from one electrode to the other. They are in ionic contact through the proton-conducting membrane 20.

Figure 4:
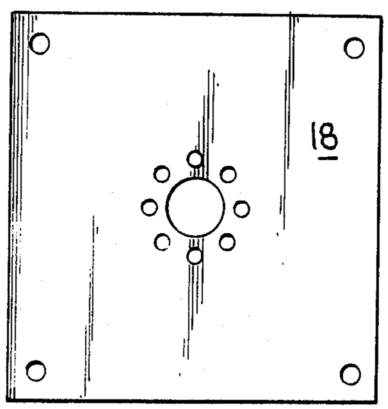
FIG. 4 is a plane view of a perforated separator/gasket assembly utilized in the cell of FIG. 1.

To achieve low ionic resistance between the sensing and counter electrodes, a perforated gasket assembly, best shown in FIG. 4, is used to maintain the membrane in the seal area hydrated. The hydrated ionomer channels in membrane 20 provide for accelerated proton-exchange/transport between the sensing and counter electrodes. The reference electrode has the same area as the sensing electrode. When assembled into hardware, the reference electrode is located in the sensor cell reservoir.

The sensor cell is potentiostated, as described by LaConti and Maget in the *Journal* to maintain the sensing electrode at approximately 1.1 V more noble than the $Pt/H_2,H+$ couple. At this potential there is no interference for $O_2$, thus air operation is practical.

Figure 6:
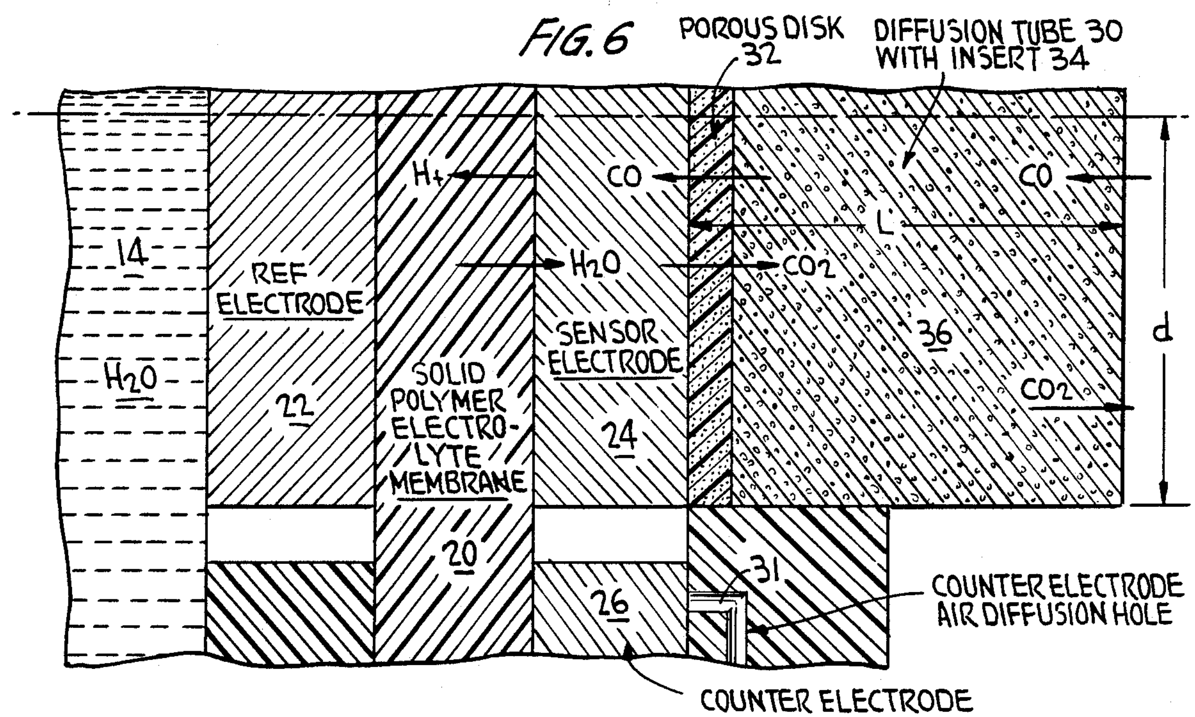
FIG. 6 is a schematic diagram of a section of the gas sensor cell according to FIG. 1.

In the preferred sensor cell configuration as shown schematically in FIG. 6, the gas to be analyzed, i.e., CO containing, diffuses to the sensor cell 10 through a diffusion tube 30 with a fixed length/diameter (L/d), having a porous metal disk 32 to attenuate flow and an integral particulate filter 36 to selectively remove probable interferants. The porous polytetrafluoroethylene (PTFE) water management film 38 of the Giner, Inc. TBE TM sensing electrode, to be described more fully hereinafter, controls and prevents water interference. The transport of reactant species is indicated by arrows in FIG. 6. Thus, the gas to be analyzed is either electrochemically oxidized or reduced at the sensing electrode and protons are laterally transported across the hydrated membrane surface and interior of the membrane by proton exchange between the sensing and counter electrodes 24 and 26. To achieve this transport, it is necessary to have a series of hydrated proton-exchange channels in the seal area between the sensing and the counter electrodes. The current generated from the electrochemical reaction and concomitant lateral proton transport/exchange is proportional to the partial pressure of reactant gas in the stream. The sensing, counter, and reference electrodes are all in separate compartments and sealed from each other, thus preventing any gas mixing or interaction. All three electrodes are ionically in contact through the proton-conducting membrane.

Having described the invention in general terms, the following presently preferred embodiments will be set forth to more specifically illustrate the invention.

Cell Description

Figure 3:
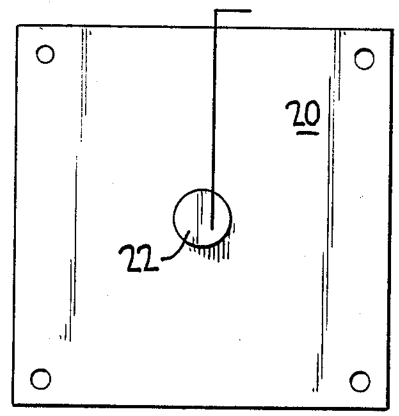
FIG. 3 is a plane view of the other side of the proton-conducting membrane showing the reference electrode utilized in the cell of FIG. 1.

A diffusion-type sensor cell, hereinafter "Cell A," was constructed having the configuration substantially as shown in FIGS. 1-6. A large Giner, Inc. TBE TM electrode was fabricated containing 20 mg/cm$^2$ Pt with 25% PTFE as a binder on a titanium screen. A sensing electrode 24, reference electrode 22, and counter electrode 26, as shown in FIGS. 2 and 3 of the drawing, were die cut from the large electrode. The reference electrode 22 was pressed onto the side of a Nafion 117 perfluorocarbon sulfonic acid membrane 20, which eventually will be used at the reservoir 12 side of the sensor cell 10. Both the sensing and counter electrodes 24 and 26 were pressed onto the other side of the membrane, with the sensing electrode directly opposite from the reference electrode. The counter electrode had a circular configuration and surrounded the sensing electrode as best shown in FIG. 2. The diameter of both the sensing and reference electrodes was 0.79 cm (0.31"). The inner and outer diameters of the circular counter electrode was 1.11 cm (0.44") and 1.59 cm (0.63"), respectively. The distance between the sensing to counter electrode edges was 0.24 cm (0.095"), and the distance between the sensing to reference electrode was 0.02 cm (0.009"). The geometric area of the electrodes was as follows:

| Configuration | Area | |
|---|---|---|
| | cm$^2$ | in$^2$ |
| Sensing | 0.50 | 0.077 |
| Counter | 0.81 | 0.125 |
| Reference | 0.50 | 0.077 |

Experimental Results

EXAMPLE 1

Cell A was tested for 30 minutes. The sensing electrode was maintained at +1.12V (versus standard hydrogen electrode, S.H.E.) using a potentiostatic circuit. During this period, counter electrode 26 was continuously exposed to ambient air, permeating through small diffusion holes 31 (diameter=0.005 cm [0.002"]) in the otherwise sealed compartment formed by diffusion tube 30. As the carbon monoxide in the feed gas passing through insert 34 was consumed at the sensing electrode according to the anodic reaction $$CO+H_2O \rightarrow CO_2+2H^+ +2e$$

the counter electrode functioned as an effective oxygen (air) electrode due to its optimized TBE™ gas diffusion configuration and the easy access to ambient air according to the reaction- $$2H^{+}+\tfrac{1}{2}O_2+2e=H_2O$$

The counter electrode steady state potential during the 30-minute time interval was +0.940V versus S.H.E., which is well above the 0.0V$H_2$ evolution value.

Figure 7:
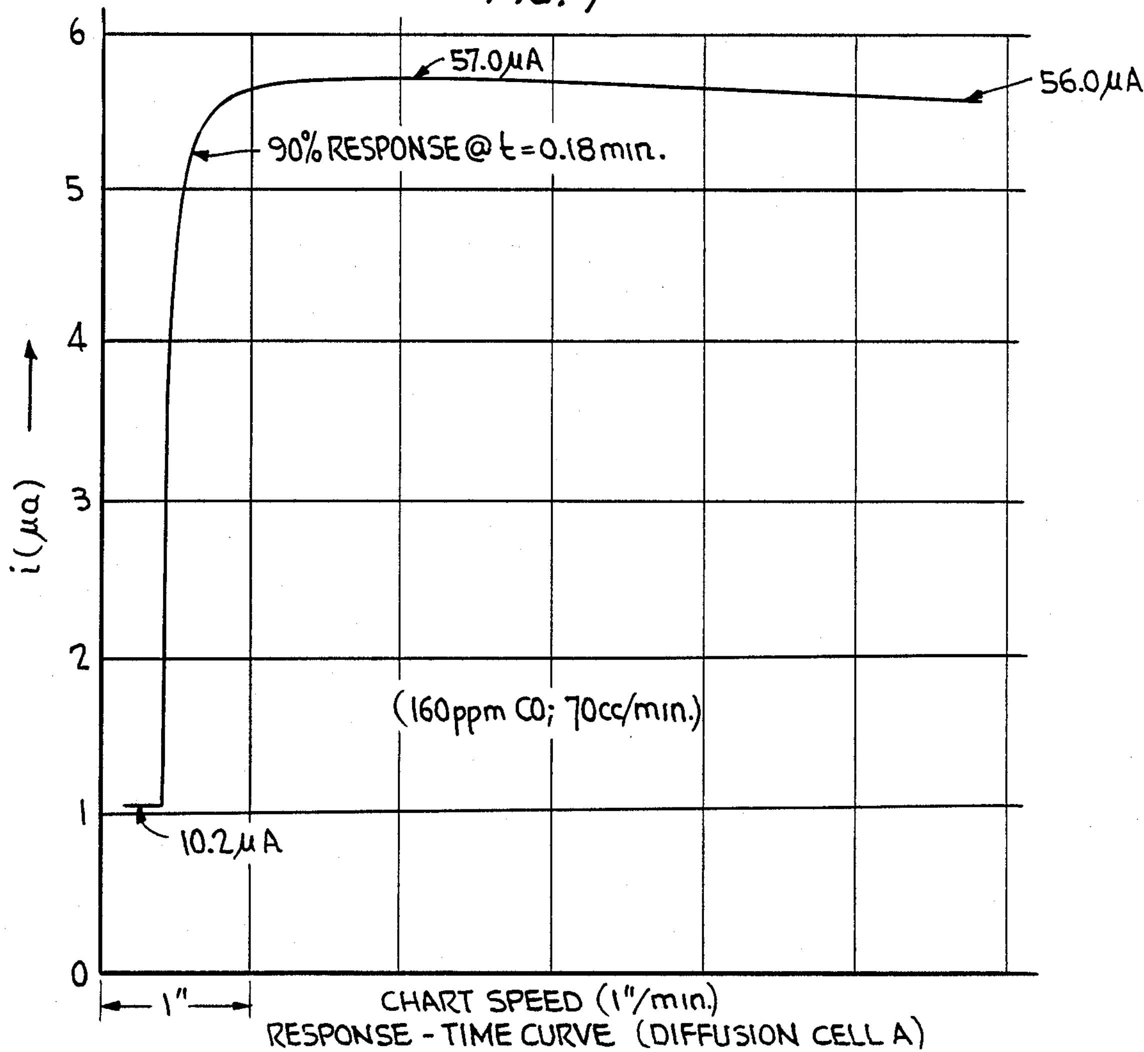
FIG. 7 is a response time curve for the gas senor cell described in Example 1 hereinafter.

It was unexpectedly found during the testing of Cell A that the response time was very fast (10–11 seconds to 90% response). Thus, a typical response-time curve for a cell as above described, having a diffusion tube with a length (L) of 1.9 cm, a diameter (d) of 0.80 cm, and a L/d of 2.4 is shown in FIG. 7. Response level when detecting 160 ppm CO in air was approximately 0.30 μa/ppm CO. The diffusion-type sensor cell of Example 1 exhibited very stable performance during 30 minutes of continuous testing.

In contradistinction, when using a cell configuration with the counter electrode located on the opposite side of the membrane with respect to the sensing electrode, the typical potential of the counter electrode is less than +0.4V versus S.H.E. when detecting 160 ppm CO. This occurs because there is only a limited quantity of dissolved oxygen (from air) in the reservoir water that covers the oxygen counter electrode. The electrode becomes gas diffusion limited (oxygen starved), and proceeds toward hydrogen potentials. Typical response time for a diffusion-type sensor cell having the sensing and counter electrodes on opposite sides of a proton-conducting solid polymer electrolyte membrane and a sensing/reference configuration with a high ionic resistance (>60 ohms) is typically 100 to 200 seconds.

The novel cell of the present invention has several advantages compared to the cell configuration of the prior art, namely: (1) the response time is faster; (2) the counter electrode functions as an efficient $O_2$ (air) reduction configuration, thus minimizing the probability of $H_2$ gas evolution; and (3) if hydrogen evolution does occur at the counter electrode when detecting high concentrations of CO, the diffusion path to the sensing electrode is considerably longer (0.24 cm versus 0.02 cm); thus, the potential for $H_2$ interference due to diffusion through the ionomer is considerably lowered.

EXAMPLE 2

Figure 5:
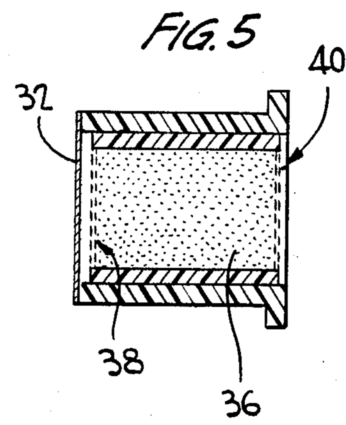
FIG. 5 is a cross-sectional view of the diffusion tube insert assembly utilized in the cell of FIG. 1.

A small gas attenuator/filter insert 36 was incorporated into diffusion tube insert 34 of Cell A described above (Example 1). A schematic of the diffusion tube insert assembly is shown in FIG. 5. The entire insert contains a porous Ni sinter disk 32 and two sheets of porous PTFE (Zitex K1064-122D or Gortex 1 micron porous PTFE) 38 and 40 to attenuate gas flow to the sensing electrode, and (2) a permanganate impregnated alumina particulate 36 sandwiched between the attenuating elements. The particulate removed easily oxidizable interferants including oxides of nitrogen, oxides of sulfur, $H_2S$, and alcohol. It also aids gas attenuation.

With the insert, the diameter of the diffusion tube , was decreased from 0.79 cm (0.31") to 0.48 cm (0.19"), and the L/d increased from 2.4 to 4.0. The response signal accordingly decreased from 0.30 to 0.13 μ/ppm CO when detecting 160 ppm CO in air at similar gas flows (approximately 70 cm³/min) across the face of the diffusion tube. Testing was conducted to determine the effect on sensor cell signal response by CO in air (160 ppm CO) flow across the face of the diffusion tube. Results are shown in the following table:

| CO in Air Flow (cm³/min) | Response (μa) Above Background |
|---|---|
| 30 | 19.4 |
| 50 | 19.6 |
| 70 | 20.3 |
| 90 | 20.9 |

The data indicate that Cell A, with the insert in the diffusion tube, (L/d) of 4, is highly flow invariant. There is only a 7.7% increase in response level when flow is increased from 30 to 90 cm³/min for this cell. The typical response time was 10 seconds. Thus, the preferred diffusion tube configuration (no gas sampling pump) of the present sensor cell shows excellent flow independent performance.

EXAMPLE 3

Cell A was modified such that a composite porous PTFE/Ni sinter structure was utilized not only in the entrance but also the exit of the diffusion tube insert described in FIG. 5. A permanganate impregnated alumina particulate was sandwiched between the porous PTFE/Ni sinter gas attenuating disks. The diffusion tube configuration with the insert had an (L/d) of 3. The signal response linearity with CO concentration was established with this sensor cell. The CO in air concentrations ranged from 0 to 150 ppm. The gases were passed over the face of the diffusion tube at a flow of 50 cm³/min. The sensor cell response (μa) as a function of CO concentration is shown in the following table:

| CO in Air Conc. (ppm) | Response (μa) Above Background |
|---|---|
| 0 | 0 |
| 15 | 4 |
| 35 | 10 |
| 52 | 14 |
| 80 | 23 |
| 120 | 30 |
| 150 | 38 |

Response level was approximately 0.27 μa/ppm CO. Response time was approximately 10 seconds.

EXAMPLE 4

Cell A was assembled with a bonded electrode/membrane cell assembly whereby a Zitex K1064-122D porous PTFE water management film was bonded to the surface of the TBE™ sensing electrode. The diffusion tube configuration, with insert, had an (L/d) of 2. The response level was 0.4 μa/ppm CO. This response level was approximately 20% lower than that observed for the same bonded electrode/membrane cell assembly without the porous PTFE water management film. The benefit of the water management film is that it improves sensor cell reproducibility by controlling liquid water film thickness/formation within the TBE™ electrode structure and the solid polymer electrolyte/electrode interfacial reaction zone, especially during temperature cycling (1° to 40° C.).

EXAMPLE 5

Figure 8:
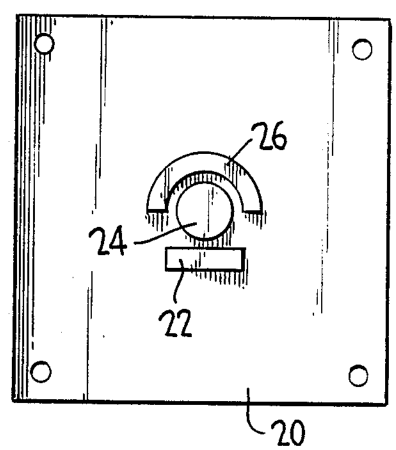
FIG. 8 is a plane view of one side of a proton-conducting membrane showing the sensing electrode, counter electrode, and reference electrode on the same side of the membrane.

Cell A was manufactured with all three TBE TM electrodes, sensing, counter and reference, bonded to the same side of the solid polymer ion-exchange membrane as shown in FIG. 8. The sensing electrode had a diameter of 1.59 cm (0.63") and active cell area of 2.0 $cm^2$. The counter and reference electrodes both had a diameter of 0.64 cm (0.25") and active cell area of 0.32 $cm^2$. The cell was fabricated with a flow-type gas chamber 40 over the sensing electrode. Diffusion tube 30 and insert 34 were not used. A 200 ppm CO in air sample was introduced into the gas chamber and directly over the sensing electrode at a flow of 70 $cm^3$/min. The response level was 1.31 μa/ppm CO.

In Examples 1 through 5 the reference electrode comprised a Pt black TBE TM structure similar to the sensing and counter electrode bonded to a hydrated Nafion 117 solid polymer electrolyte ion-exchange membrane. The Pt black TBE TM structure was fabricated from a commercial (Engelhard) fuel cell grade catlyst/Teflon particulate, supported with expanded Ti mesh. The surface area of the Pt black catalyst was approximately 20 $m^2/g$. In this configuration the Pt black structure equilibrated with the dissolved oxygen in the water of the cell reservoir to form a Pt/$O_2$ (gas), $H^+$ (solid electrolyte) couple. The rest potential of this electrode structure was approximately 1.06 V (versus a standard hydrogen electrode, S.H.E.). The sensing electrode was potentiostated at +120 mV above the reference Pt/$O_2$ (gas) electrode.

In the above examples, the integrally bonded Pt/$O_2$ (gas) reference electrode structure can be replaced with other electrodes. Two illustrative replacement electrodes are an integrally bonded platinum dioxide electrode and a dynamic hydrogen electrode (D.H.E.). A description of these two reference electrode structures and their comparative performance in an integrally bonded electrode/solid electrolyte cell are set forth in Examples 6 and 7.

EXAMPLE 6

Platinum Dioxide Electrode-The particulate catalyst for use in this electrode was prepared by the Adam's method (R. Adams and R. L. Schriner, *Journal of the American Chem. Soc.*, 45, 217, incorporated herein by reference) to obtain a very high surface area (80 to 160 $m^2/g$) particulate material. The material was distinctly light brown in color and had the stoichiometry $PtO_2$. The catalyst was fabricated into a TBE TM electrode structure with Teflon and a support mesh as described hereinbefore, and bonded to an ion-exchange membrane on the side opposite that containing the integrally bonded sensing electrode and counter electrode. The rest potential of the platinum dioxide electrode was 1.02 V (versus the S.H.E.). The response level of a diffusion sensor cell containing the $PtO_2$ reference electrode when detecting 200 ppm CO in air was 0.45 μa/ppm CO. The response time was less than one minute. Sensor cells that were similarly constructed with the exception that they had a reference Pt black TBE TM electrode in equilibrium with dissolved oxygen as in Examples 1 through 5, gave a response level of 0.35 to 0.50 μa/ppm.

EXAMPLE 7

Dynamic Hydrogen Electrode-The electrodes and hardware configuration for this sensor cell were similar to that shown in FIG. 6. Three Pt black TBE TM structures were integrally bonded to the solid polymer electrolyte membrane and used as the sensor, counter and reference electrode. The unique feature of this cell was that a small DC current (0.1 mA) was passed between the bonded reference electrode on the reservoir side of the membrane and bonded counter electrode on the other side of the membrane—located on the same side of the membrane as the sensing electrode. The negative terminal of the battery was connected to the reference electrode which was located in a reservoir flooded with water. The integrally bonded reference electrode was driven to hydrogen evolution to form a very stable and reproducible dynamic hydrogen electrode (D.H.E.). The integrally bonded counter electrode was driven to oxygen evolution. The D.H.E. electrical circuit is completely isolated so that it had no interaction with the CO sensor cell potentiostatic circuit. A sensor cell fabricated with the D.H.E. configuration and potentiostated at 1.15 V above the D.H.E. gave a response level of 0.42 μa/ppm when detecting 200 ppm CO in air. Response time was within one minute. The major advantage of the integrally bonded D.H.E. reference electrode configuration is the highly stable and reversible reference voltage it provides for the potentiostated sensor cell.

Both of the reference electrode structures used in Examples 6 and 7 can be used in ambient air or atmospheres having little or no oxygen, offering an advantage over a Pt/$O_2$ gas reference which can be used only in an oxygen-containing environment (10–100% oxygen). Also, the general voltage stability and reversibility of both these electrodes is high, especially the D.H.E.

The diffusion-type sensor cell configuration containing the sensing and counter electrode in intimate contact with the same side of a proton-conducting membrane according to the present invention can be used to detect a wide range of readily oxidizable or reducible species. Thus, cells were prepared according to the present invention as shown in FIGS. 1–6 of the drawing, and operated for the detection of gases as shown in Table 1. Table 1 sets forth the gas to be detected, the catalyst of the sensing electrode, the potentiostatic voltage of the cell, the electrochemical reaction, range over which the gas can be detected, the interfering species, and the integral diffusion filter which was employed to remove the interfering species. Table 1 is as follows:

TABLE 1

Applications Of Diffusion-Type Cell/With Sensing/Counter Electrode Bonded To The Same Side Of A Proton Membrane

| Gas To Be Detected | Sensing Electrode | Potentiostatic Voltage (Vs.SHE Electrode) | Electrochemical Reaction | Range (ppm) | Interfacing Species | Integral Diffusion Filter to Remove Interfering Species |
|---|---|---|---|---|---|---|
| Carbon Monoxide | Pt | +1.15 | $CO + H_2O = CO_2 + 2H^+ + 2e$ | 0–1000 | NO, $SO_2$, $H_2S$ | $KMnO_4$ on Alumina |
| Nitric Oxide | Graphite | +1.30 | $NO + H_2O = NO_2 + 2H^+ + 2e$ | 0–100 | $SO_2$, $H_2S$ | Triethanolamine (TEA) |
| Nitrogen | Graphite | 0.75 | $NO_2 + 2H^+ + 2e =$ | 0–5 | $SO_2$, $H_2S$ | $Hg^{++}$ Salts - |

TABLE 1-continued

| | | Applications Of Diffusion-Type Cell/With Sensing/Counter Electrode Bonded To The Same Side Of A Proton Membrane | | | | |
|---|---|---|---|---|---|---|
| Gas To Be Detected | Sensing Electrode | Potentiostatic Voltage (Vs.SHE Electrode) | Electrochemical Reaction | Range (ppm) | Interfacing Species | Integral Diffusion Filter to Remove Interfering Species |
| Dioxide | | | $NO + H_2O$ | | | Immobilized |
| Alcohol | Pt—Ir | +1.3 | $C_2H_5OH + H_2O = CH_3COOH + 4H^+ + 4e$ | 0–4000 | Thio Compounds, i.e., garlic, onions | Activated Carbon |
| Hydrogen | Pt or Silicone Covered Pt | +1.1 | $2H_2 = 4H^+ + 4e$ | 0–20,000 | $SO_2$, $H_2S$, NO, CO | $KMnO_4$ on Alumina Hopcalite |
| Oxides of Sulfur | Graphite | +1.0 | $SO_2 + H_2O = SO_3 + 2H + 2e$ | 0–2000 | $H_2S$ | $Ag^+$on Alumina $Pb^{++}$Alumina |
| Hydrogen Sulfide | Graphite | +1.0 | $H_2S + 4H_2O = H_2SO_4 + 8H^+ + 8e$ | 0–100 | $SO_2$ | CaO, $HCO_3$ |
| Chlorine/ Bromine | Graphite or Platinum | +0.7-1.2 | $Cl_2 + 2H^+ + 2e = 2HCl$ | 0–5 | $SO_2$, $H_2S$ | $Hg^{++}$Salts - Immobilized |
| Oxygen | Pt—Au or Silicone Covered Pt—Au | +0.7 | $O_2 + 4H^+ + 4e = 2H_2O$ | 2000–200,000 | None at These High CO Levels | $KMnO_4$ on Alumina Activated Carbon |

Representative results of detecting gases and vapors shown in Table 1 are set forth in Examples 8 and 9.

EXAMPLE 8

Chlorine Detection-Four sensor cells were evaluated for detection of $Cl_2$. Three of the four cells contained TBE TM carbon black catalyzed sensing electrodes with low carbon loadings, both as received and modified by impregnation with varying levels of liquid Nafion ionomer, while the fourth cell contained a platinoid black sensing electrode. These TBE TM sensing electrodes were all integrally bonded to the electrolyte membrane.

The cell configuration and the results of the tests with approximately 5 ppm $Cl_2/N_2$ are summarized in Table 2 as follows:

TABLE 2

| | | Summary of Cell Configurations And Response To 5 ppm $Cl_2/N_2$ | | |
|---|---|---|---|---|
| Cell # | Sensing Electrode | Potential Range Tested (mV vs. SHE) | $Cl_2$ Response (μA/ppm) | Time to 90% of Signal (sec.) |
| 1 | 1.25 mg/cm$^2$ carbon black/ no Nafion | 700 to 850 | 1-2 | >60 |
| 2 | 1.6 mg/cm$^2$ carbon black/ high Nafion | 700 to 850 | <0.5 | — |
| 3 | 1.6 mg/cm$^2$ carbon black/ low Nafion | 750 to 825 | ≈2 | ≈20 |
| 4 | Pt black/ no Nafion | 1050 to 1200 | 2.5 | 40-60 |

The best results were obtained with Cells 3 and 4 containing a 1.6 mg/cm$^2$ carbon black electrode impregnated with a small amount of Nafion ionomer and a platinoid black electrode, respectively. The response level was slightly higher for Cell 4, approximately 2.5 μa/ppm $Cl_2$ compared to 2 μa/ppm for Cell 3, but the response was faster for Cell 3, obtaining 90% of the final signal in approximately 20 seconds. A comparison of the results for Cells 1–4 indicates that a small amount of Nafion ionomer on the sensing electrode surface improves both the $Cl_2$ response level and the time of the response, but that larger amounts of impregnated Nafion ionomer decrease the response.

EXAMPLE 9

Ethanol Vapor Detection - Ethanol vapor was readily detected using a sensor cell configuration similar to that shown in FIG. 6. The sensor cell was potentiostated at 1.10 V versus SHE. The response versus concentration data are presented in the Table 3 and indicate good linearity and sensitivity for ethanol vapor up to the blood intoxification limit of 0.1% (1000 ppm). Response level for alcohol vapor was approximately 0.34 μa/ppm over the range 0 to 1000 ppm.

TABLE 3

| Sensor Response for Alcohol | |
|---|---|
| Concentration (ppm) | Response (microamps) |
| 100 | 24 |
| 200 | 69 |
| 500 | 190 |
| 1000 | 350 |

In the above examples, various modifications can be made in the cells as long as the sensing electrode and counter electrode are on the same side of the hydrated proton-conducting membrane. Thus, the solid polymer electrolyte ion-exchange membrane 20 can be any ion-exchange membrane which permits passage of positively charged ions, i.e., cations, and rejects and blocks passage of negatively charged ions, i.e., anions. The hydrogen ions produced at the sensing electrode through oxidation of, for example, carbon monoxide must be transported through the ion-exchange membrane to the counter electrode where the ions are reduced by the addition of electrons to produce molecular hydrogen or water. These membranes preferably are perfluorocarbon sulfonic acid membranes because of their excellent ion-exchange capacity, high staility, good resistance to acids and strong oxidants, and excellent thermal stability. In addition, the perfluorocarbon sulfonic acid membranes are essentially invariant with time and, thus, will not degrade. A preferred form of such cation membrane is one in which the polymer is a hydrated copolymer of polytetrafluoroethylene (PTFE) and polysulfonyl fluoride vinyl ether containing pendant sulfonic ($SO_3$-H+) acid groups. The sulfonic groups are chemically bound to the perfluorocarbon backbone so that the concentration of the electrolyte remains fixed. After equilibrating the membrane by hydrating it through soaking in 100° C. water for 30 minutes, the structure of the sulfonated perfluorocarbon is as follows:

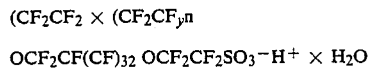

The ionic conductivity of this particular solid polymer electrolyte, which is sold by the duPont Company unders its trade designation "Nafion," is provided by the mobility of the hydrated hydrogen ions ($H+x\ H_2O$).

Electrodes 22, 24 and 26 are preferably the Giner TBE TM electrodes which comprise a mixture of electrocatalyst such as Group VIII metal catalysts dispersed on a carrier material such as carbon in admixture with polytetrafluoroethylene (PTFE). The mixture of electrocatalyst and PTFE can be pressed on or into a current-conducting metal screen such as a titanium or nickel screen, or can be pressed at one surface of a hydrophobic film or sheet such as a PTFE sheet. The preferred catalysts for use herein, because of their ability to readily oxidize and reduce gases such as carbon monoxide, oxygen and the like, are platinum or palladium catalysts or alloys of platinum such as described, for example, in Jalan, U.S. Pat. application Ser. No. 780,587 filed Sept. 26, 1985. Other electrocatalysts, in any configuration compatible when in intimate contact with a proton-conducting membrane, can be utilized. Also, the sensor cell can be fabricated using Nafion perfluorosulfonic acid ionomer in tubular form (Nafion 815), having a diameter that is convenient for a cathetor mounted device. Both the sensing and counter TBE TM electrodes are to be in intimate contact with the same side of the tubular membrane. Additionally, it will be appreciated that while it is necessary to hydrate the proton-conducting membrane, it is not essential to have a water reservoir of the type shown in FIG. 1 of the drawing, although a reservoir is preferred. The membrane can be hydrated using water vapor instead of liquid water so long as the relative humidity in the vicinity of the cell membrane is maintained above 80%. A water vapor transport film can be inserted between the cell membrane and the water source, allowing use of impure water feeds (with salts, glycols, etc.) or body perspiration as a source of water vapor. A potential advantage of using impure water such as a water/glycol solution as a source of water vapor is that specific water/glycol mixtures do not readily freeze, permitting use of these sensors at very low operating temperatures. The water vapor transport film will not allow direct contact of the water/glycol solution with the cell electrode components. The water transport membrane will allow only the passage of pure water vapor. Further, the diffusion tube shown in FIG. 1 can be in various configurations and constructions, with it only being necessary that the counter electrode and the sensing electrode are physically separated from each other so as to prevent gas mixing or interaction while still having ionic transport between the electrodes.

As will be apparent to one skilled in the art, various modifications can be made within the scope of the aforesaid description. Such modifications being within the ability of one skilled in the art form a part of the present invention and are embraced by the appended claims.

It is claimed:

1. A diffusion-type gas sensor cell for quantitatively detecting a gas in a fluid medium comprising a proton-conducting solid polymer electrolyte membrane, a sensing electrode in contact with a first surface of said membrane; a counter electrode in contact with the same surface of said membrane as said sensing electrode, and a reference electrode in contact with said membrane; an electronic circuit means coupling said sensing, reference and counter electrodes for maintaining the potentials at said electrodes at predetermined levels; and means for measuring the current flow between said counter and sensing electrodes as a function of the concentration of a gas being detected in a fluid medium.

2. The cell of claim 1 wherein said reference electrode is directly opposite from said sensing electrode on the opposite side of said membrane and is of the same area.

3. The cell of claims 1 and 2 wherein said sensing electrode is circular and said counter electrode is spaced from and surrounds said sensing electrodes.

4. The cell of claim 1 wherein said reference electrode is on the same side of said membrane as said sensing and counter electrodes.

5. The cell of claim 1 wherein said electrodes comprise a catalytic mixture including a Group VIII metal catalyst and polytetrafluoroethylene particles in contact with a metal support screen.

6. The cell of claim 5 wherein said electrode has a hydrophobic sheet on the surface of the electrode not in contact with said membrane.

7. The cell of claim 6 wherein said hydrophobic sheet is a sheet of gas-permeable polytetrafluoroethylene.

8. The cell of claim 5 wherein the catalyst is platinum black and the metal support screen is titanium mesh.

9. The cell of claim 5 wherein the catalyst is platinum dioxide.

10. The cell of claim 5 wherein the reference electrode is a dynamic hydrogen electrode.

11. The cell of claim 5 wherein said catalytic mixture includes an ionomer of a perfluorocarbon sulfonate.

12. The method of detecting a gas in an atmosphere comprising subjecting the sensor cell of claim 1 to an atmosphere containing a gas to be detected and determining the amount of said detected gas with said sensor cell.

13. The method of claim 12 wherein the gas is carbon monoxide.

14. The method of claim 12 wherein the gas is chlorine.

15. The method of claim 12 wherein the gas is ethanol.

16. A gas-diffusing sensor cell for measuring the level of a gas in a fluid medium comprising water reservoir means, a proton-conducting membrane, a reference electrode in intimate contact with one surface of said membrane and in contact with water in said reservoir means; a gas sensing electrode in contact with the second surface of said membrane and positioned directly opposite of said reference electrode; and a counter electrode in contact with said membrane surrounding said sensing electrode; means for maintaining said sensing and counter electrodes separated from each other and forming a compartment around said electrodes; means for distributing air to said counter electrode; means for distributing a fluid medium containing a gas to be detected and measured to said sensing electrode; potentiostatic circuit means for maintaining the sensing, reference and counter electrodes at predetermined potentials; and means for measuring the current flowing between the counter and sensing electrodes as a function of the gas being detected in said fluid medium.

17. The cell of claim 16 wherein said electrodes comprise a catalytic mixture including a Group VIII metal catalyst and polytetrafluoroethylene particles in contact with a metal support screen.

18. The cell of claim 17 wherein said electrode has a hydrophobic sheet on the surface of the electrode not in contact with said membrane.

19. The cell of claim 18 wherein said hydrophobic sheet is a sheet of gas-permeable polytetrafluoroethylene.

20. The cell of claim 17 wherein the catalyst is platinum black and the metal support screen is titanium mesh.

21. The cell of claim 17 wherein the catalyst is platinum dioxide.

22. The cell of claim 17 wherein the reference electrode is a dynamic hydrogen electrode.

23. The cell of claim 17 wherein said catalytic mixture includes an ionomer of a perfluorocarbon sulfonate.

24. The method of detecting a gas in an atmosphere comprising subjecting the sensor cell of claim 16 to an atmosphere containing a gas to be detected and determining the amount of said detected gas with said sensor cell.

25. The method of claim 24 wherein the gas is carbon monoxide.

26. The method of claim 24 wherein the gas is chlorine.

27. The method of claim 24 wherein the gas is ethanol.

* * * * *